(12) United States Patent
Gorelick et al.

(10) Patent No.: US 12,226,486 B2
(45) Date of Patent: *Feb. 18, 2025

(54) METHOD FOR BOWEL PREPARATION

(71) Applicant: MSM Innovations, Inc., Weston, CT (US)

(72) Inventors: Steven Gorelick, Danbury, CT (US); Michael Schiffman, Weston, CT (US); Melody Olmstead, New Milford, CT (US); Adam Gorelick, Woodbridge, CT (US)

(73) Assignee: MSM Innovations, Inc., Weston, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/455,930

(22) Filed: Aug. 25, 2023

(65) Prior Publication Data
US 2023/0405128 A1 Dec. 21, 2023

Related U.S. Application Data

(63) Continuation of application No. 17/342,983, filed on Jun. 9, 2021, now Pat. No. 11,771,768, which is a continuation of application No. 16/394,877, filed on Apr. 25, 2019, now Pat. No. 11,058,774, which is a continuation of application No. 15/793,257, filed on Oct. 25, 2017, now abandoned, which is a continuation of application No. 15/456,028, filed on Mar. 10, 2017, now abandoned, which is a continuation of application No. 15/165,948, filed on May 26, 2016, now Pat. No. 9,629,917, which is a continuation of application No. 14/963,616, filed on Dec. 9, 2015, now Pat. No. 9,352,044, which is a continuation of application No. 13/708,430, filed on Dec. 7, 2012, now Pat. No. 9,238,075.

(60) Provisional application No. 61/568,131, filed on Dec. 7, 2011.

(51) Int. Cl.
| A61K 47/42 | (2017.01) |
| A61K 9/00 | (2006.01) |
| A61K 9/08 | (2006.01) |
| A61K 33/04 | (2006.01) |
| A61K 33/14 | (2006.01) |
| A61K 33/42 | (2006.01) |
| A61K 47/10 | (2017.01) |
| A61K 47/26 | (2006.01) |
| A61K 47/34 | (2017.01) |
| A61K 47/02 | (2006.01) |
| A61K 47/12 | (2006.01) |

(52) U.S. Cl.
CPC ............ *A61K 47/42* (2013.01); *A61K 9/0053* (2013.01); *A61K 9/0095* (2013.01); *A61K 9/08* (2013.01); *A61K 33/04* (2013.01); *A61K 33/14* (2013.01); *A61K 33/42* (2013.01); *A61K 47/10* (2013.01); *A61K 47/26* (2013.01); *A61K 47/34* (2013.01); *A61K 47/02* (2013.01); *A61K 47/12* (2013.01)

(58) Field of Classification Search
CPC ........ A61K 47/02; A61K 47/10; A61K 47/12; A61K 47/26; A61K 47/42; A61K 9/0095; A61K 9/0053; A61K 33/42

See application file for complete search history.

(56) References Cited

U.S. PATENT DOCUMENTS 7,169,381 B2 * 1/2007 Barras .................. A61K 9/0095
424/78.01

OTHER PUBLICATIONS

Kurihara, K.; Beidler, L.M. "Mechanism of the Action of Taste-modifying Protein" Nature 1969, 222, 1176-1179 (Year: 1969).*

Kumler, W.D.; Daniels, T.C. "Titration Curves and Dissociation Constants of l-Ascorbic Acid (Vitamin C) and Diethyl Dihydroxymaleate" J. Am. Chem. Soc., 1935, 57 (10), pp. 1929-1930 (Year: 1935).*

Capitanio, A. et al. "Mixing Taste Illusions: The Effect of Miraculin on Binary and Trinary Mixtures" Journal of Sensory Studies 26 (2011) 54-61 (published online Feb. 1, 2011). (Year: 2011).*

* cited by examiner

*Primary Examiner* — Andrew S Rosenthal
(74) *Attorney, Agent, or Firm* — Leason Ellis LLP

(57) ABSTRACT

The present invention provides methods for facilitating cleansing of the gastrointestinal tract of a patient prior to a diagnostic, surgical or therapeutic procedure. The methods can improve patient compliance, and thus, efficacy of the preparation. Specifically, the present methods make the gastrointestinal tract preparation composition palatable for the patient to consume. For example, for a patient preparing to undergo colonoscopy, the present methods make the bowel preparation solution taste significantly less salty.

22 Claims, 7 Drawing Sheets

Figure 2

PATIENT QUESTIONNAIRE PRIOR TO ADDITION OF FLAVOR PACK AND USE OF MIRACLE FRUIT

1. Please rate the sweetness of the preparation on the 0 – 100 scale below.
   Zero

0----10----20----30----40----50----60----70----80----90----100

2. Please rate the saltiness of the preparation on the 0 – 100 scale below.

0----10----20----30----40----50----60----70----80----90----100

3. Please rate the overall palatability of the preparation on the 0 – 100 scale below.

PATIENT QUESTIONNAIRE AFTER USE OF MIRACLE FRUIT AND ADDITION OF FLAVOR PACK

1. Please rate the sweetness of the preparation on the 0 – 100 scale below.

0----10----20----30----40----50----60----70----80----90----100

2. Please rate the saltiness of the preparation on the 0 – 100 scale below.

0----10----20----30----40----50----60----70----80----90----100

3. Please rate the overall palatability of the preparation on the 0 – 100 scale below.

Post-Preparation Patient Questionnaire (to be completed after completion of the preparation)

1. Please indicate the percentage of the preparation that you completed.

0% ---------------25%---------------50%----------------75%--------------100%

2. How many berry tablets do you have left over after completion of the preparation?

1        2        3        4        5        6

3. Did you think that the use of the flavor pack and the miracle fruit helped in you completion of the preparation?

YES                NO

Palatability, Saltiness or Sweetness Rating

Palatability, Saltiness or Sweetness Rating

METHOD FOR BOWEL PREPARATION

CROSS REFERENCE TO RELATED APPLICATIONS

This application is a continuation of U.S. patent application Ser. No. 17/342,983 filed Jun. 9, 2021, which is a continuation of U.S. patent application Ser. No. 16/394,877 filed Apr. 25, 2019, which is a continuation of U.S. patent application Ser. No. 15/793,257 filed Oct. 25, 2017, which is a continuation of U.S. patent application Ser. No. 15/456,028 filed on Mar. 10, 2017, which is a continuation of U.S. patent application Ser. No. 15/165,948 filed on May 26, 2016, now U.S. Pat. No. 9,629,917, which is a continuation of U.S. patent application Ser. No. 14/963,616 filed on Dec. 9, 2015, now U.S. Pat. No. 9,352,044, which is a continuation of U.S. patent application Ser. No. 13/708,430 filed on Dec. 7, 2012, now U.S. Pat. No. 9,238,075, which claims the benefit of U.S. Provisional Application No. 61/568,131 filed on Dec. 7, 2011. The entire contents of all of these applications are incorporated by reference in their entirety.

The present invention relates to methods for cleansing the gastrointestinal tract of a patient prior to a diagnostic, surgical or therapeutic procedure. In particular, this invention makes the gastrointestinal tract preparation composition palatable.

BACKGROUND OF THE INVENTION

Colorectal cancer is the third most common cancer amount both men and women in the world. Early detection of colorectal cancer great improves the chances of a cure. Colonoscopies are widely recognized as the gold standard for colorectal cancer screening. Rex et al., Colorectal cancer prevention 2000: Screening recommendations of the American College of Gastroenterology. *Am J. Gastroenterol.* 2000; 95: 868-877. Colonoscopies are also frequently used to diagnose many other gastrointestinal pathologies.

Despite the effectiveness of colonoscopies, compliance is often an issue among patients, mainly due to the bowel preparation procedure where the patient is required to drink large volumes of a foul-tasting solution. For the colonoscopy test to be performed properly, the colon must be free of solid matter. Thus, prior to undergoing a colonoscopy, the patient needs to ingest bowel preparation solutions to empty the bowel. The preparations typically contain large amounts of polyethylene glycol and electrolytes (e.g., sodium chloride, sodium bicarbonate, and/or potassium chloride). A large amount (e.g., 4 liters) of this salty and foul-tasting solutions must be taken orally to cleanse the bowel. The bowel preparation procedure is often described as very unpleasant by colonoscopy recipients. U.S. Patent Publication No. 20090053304.

Inadequate preparations are responsible for up to ⅓ of all incomplete procedures, preclude up to 10% of examinations, and negatively impact the rate of polyp and adenoma detection. Technology Status Evaluation Report: Colonoscopy Preparation, *Gastrointestinal Endoscopy*, 2009, 69(7): 1201-1209. Because of the importance of proper cleansing of the colon, there has been an increased focus on the palatability of the solution as a factor of patient compliance. The Prep Is Worse Than The Procedure, *Harvard Health Newsletters*, Jan. 1, 2010.

The ideal bowel preparation is safe, effective and acceptable to patients with negligible discomfort. Because it is safer and more effective than other prep solutions, polyethylene glycol (PEG) solution has been used as the so-called "gold standard" for colonoscopy. However, despite the fact that PEG solutions are well tolerated by patients, 5%-15% of patients do not complete the preparation because of poor palatability and/or large volume. R H Hawes et al., Consensus Document on Bowel Preparation before Colonoscopy, *Gastrointestinal Endoscopy* 2006, 63(7): 894-909. Efforts have been made to make bowel preparation solutions more palatable with the addition of flavorings. For example, PEG solutions are available in multiple flavors, such as cherry, citrus-berry, lemon-lime, orange and pineapple. Sulfate salts have been removed from gastrointestinal tract preparation solutions such as HalfLytely® and NuLYTELY® resulting in a less salty taste and a less pungent "rotten egg" smell". Water, ginger ale, Gatorade, CrystalLite, and carbohydrate-electrolyte solutions have also been used to improve the taste of these solutions. However, flavoring packages do not significantly change palatability in terms of the saltiness and overall taste. Furthermore, improved flavor does not necessarily equate to improved tolerance. In fact, when flavoring additions is added, special care must be taken to avoid altering the osmolarity of the preparation or adding substrates to the preparation which can metabolize into explosive gases or alter the amount of water and salts absorbed. R H Hawes et al., Consensus Document on Bowel Preparation before Colonoscopy, *Gastrointestinal Endoscopy*, 2006, 63(7):894-909.

Therefore, there is still a need for development of palatable bowel preparation compositions that would achieve effective cleansing with improved tolerability and reduced adverse effects.

Miraculin is a glycoprotein derived from the miracle fruit plant (*Richadella dulcifica* or *Synepalum dulcificum*) native to Ghana, West Africa. Although not sweet itself, miraculin has an effect of modifying the sourness of a food to taste sweet without the addition of sugar or artificial sweeteners. Sour substances such as lemons and limes taste sweet after a person eats the flesh of the berry or after freeze-dried extracts of miraculin are dissolved on the person's tongue. This sweet effect can last up to one to two hours or longer.

Miraculin modifies the perception of taste by making the sweet receptors more responsive to acids instead of only to sugars and other sweet substances. R H Cagan, Chemostimulatory Protein: A New Type of Taste Stimulus, *Science* 181(94):32-5 (Jul. 6, 1973); Ravi Kant, Sweet Proteins-Potential Replacement for Artificial Low Calorie Sweeteners, *Nutrition Journal*, 2005, 4:5. Miraculin is also effective in inducing a taste of sweetness in mixtures that includes a salty tastant. Capitanio et al., Mixing Taste Illusions: The Effects of Miraculin on Binary and Trinary Mixtures, *Journal of Sensory Studies*, 26 (2011) 54-61. However, it was also reported that, although the miracle fruit made sour foods taste sweet, it slightly enhanced other flavors, such as the degree of saltiness. See, Miracle Fruit Research at Dulci Berry Website, 2012.

The present invention provides methods to use, e.g., miraculin or miracle berry, to make the gastrointestinal tract preparation composition palatable. The use of the present invention is expected to have better patient compliance resulting in the ingestion of the complete bowel preparation and cleaner colonic mucosa.

SUMMARY

The present invention provides for a method for cleansing the gastrointestinal tract of a patient comprising the steps of: (a) determining the pH of a gastrointestinal tract preparation composition which has a salty taste, and adjusting the pH to range from about 3 to about 6.4 if necessary; (b) providing a taste-modifying substance to the patient; and (c) administering orally the gastrointestinal tract preparation composition to the patient, wherein the salty taste of the gastrointestinal tract preparation composition is reduced by at least about 20%, at least about 30%, at least about 50%, or at least about 70% compared to the salty taste of the gastrointestinal tract preparation composition had the taste-modifying substance not been provided. The step to determine the pH of the gastrointestinal tract preparation composition may be carried out prior to or after the step of providing a taste-modifying substance to the patient. The desired pH may range from about 4 to about 6.4. The desired pH may range from about 4.5 to about 5. In a specific embodiment, the desired pH is about 4.8.

For example, the present invention provides methods for cleaning the intestine (e.g., the colon). The present gastrointestinal tract preparation composition may be a bowel preparation solution.

The gastrointestinal tract may be cleansed prior to carrying out a diagnostic, therapeutic and/or surgical procedure on the patient. For example, the gastrointestinal tract is cleansed prior to an endoscopy, such as a colonoscopy or sigmoidoscopy. The gastrointestinal tract may be cleansed prior to a barium enema examination, capsule endoscopy, colon surgery or gastrointestinal tract surgery.

Non-limiting examples of the taste-modifying substance include thaumatin, monellin, mabinlin, brazzein, pentadin, curculin, neuculin, miraculin and mixtures thereof. The taste-modifying substance can be provided in the form of a capsule, a tablet, a pill, granules, powders, a pellet, a solids mixture, a solution, a dispersion, an emulsion, a paste, an extract, or an isolate from a natural source.

The taste-modifying substance may be a sour taste-modifying agent, such as miraculin. Miraculin can be given in any suitable form, such as miracle fruit, flesh of miracle fruit, miracle fruit granules, miracle berry, miracle berry extracts, miracle berry tablets, miracle fruit tablets, or miraculin produced by a genetically modified organism.

The taste-modifying substance may be provided to the patient from about 1 minute to about 2 hours, from 5 minutes to about 1 hour, from about 5 minutes to about 30 minutes, from about 1 minute to about 5 minutes or from about 10 minutes to about 15 minutes before the gastrointestinal tract preparation composition is administered.

The pH of the gastrointestinal tract preparation composition may be adjusted by at least an inorganic acid or an organic acid. For example, the acids include, but are not limited to, citric acid, acetic acid, ascorbic acid, phosphoric acid, malic acid, succinic acid, formic acid, fumaric acid, maleic acid, or mixtures thereof. The pH of the gastrointestinal tract preparation composition may also be adjusted by ammonium hydroxide, sodium carbonate, potassium carbonate, sodium bicarbonate, carbon dioxide, or mixtures thereof.

The gastrointestinal tract preparation composition may contain a potassium salt, a sodium salt, a calcium salt, an ammonium salt or mixtures thereof. For example, the gastrointestinal tract preparation composition comprises sodium chloride, potassium chloride, and sodium bicarbonate (sodium hydrogen carbonate), sodium sulfate or mixtures thereof. The gastrointestinal tract preparation composition may include at least one sodium phosphate. The gastrointestinal tract preparation composition may contain at least one alkali metal (e.g., sodium and potassium) salt, and/or at least one alkaline earth metal (e.g., magnesium or calcium) salt.

The gastrointestinal tract preparation composition may comprise polyethylene glycol (PEG). The gastrointestinal tract preparation composition may be a solution. The volume of the gastrointestinal tract preparation composition can range from about 0.1 liters to about 5 liters or from about 1 liter to about 4 liters.

BRIEF DESCRIPTION OF THE DRAWINGS

FIG. 2 is a sample patient questionnaire after tasting the bowel preparation solution prior to addition of a flavor pack and use of miracle fruit.

FIG. 3 is a sample patient questionnaire after tasting the bowel preparation solution with use of miracle fruit and addition of a flavor pack to the bowel preparation solution.

FIG. 4 is a sample of post-preparation patient questionnaire (i.e., to be completed after completion of the preparation).

DETAILED DESCRIPTION OF THE INVENTION

Figure 1:
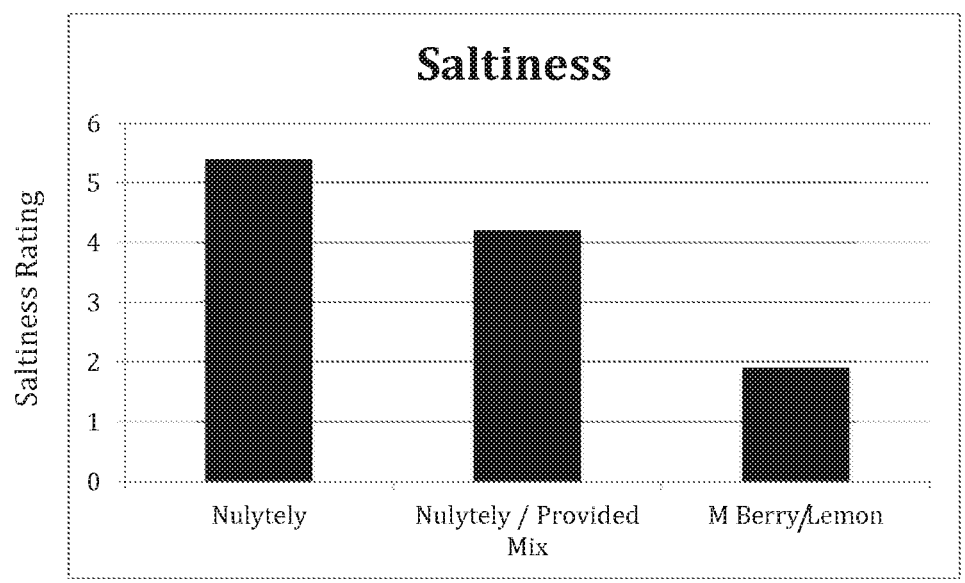
FIG. 1 is a graph demonstrating the average perception of saltiness of the bowel preparation solution for the subjects with and without miracle berry tablets.

The present invention provides methods for cleansing the gastrointestinal tract of a patient prior to a diagnostic, surgical or therapeutic procedure. The methods can improve patient compliance, and thus, efficacy of the preparation. Specifically, the present methods make the gastrointestinal tract preparation composition palatable for the patient to consume. For example, for a patient preparing to undergo colonoscopy, the present methods make the bowel preparation solution taste significantly less salty.

The present invention provides a method for cleansing the gastrointestinal tract of a patient. The method has the following steps: (a) determining the pH of a gastrointestinal tract preparation composition, and adjusting the pH to range from about 3 to about 6.4 if necessary (i.e., the pH needs to be adjusted if the pH of the preparation composition falls outside of the desired range, e.g., from about 3 to about 6.4, or other ranges as disclosed herein); (b) providing a taste-modifying substance to the patient; and (c) administering orally the gastrointestinal tract preparation composition to the patient.

The present invention further provides a method for cleansing the gastrointestinal tract of a patient. The method has the following steps: (a) determining the pH of a gastrointestinal tract preparation composition which has a salty taste, and adjusting the pH to range from about 3 to about 6.4 if necessary (i.e., the pH needs to be adjusted if the pH of the preparation composition falls outside of the desired range, e.g., from about 3 to about 6.4, or other ranges as disclosed herein); (b) providing a taste-modifying substance to the patient; and (c) administering orally the gastrointestinal tract preparation composition to the patient, wherein the salty taste of the gastrointestinal tract preparation composition is reduced by at least about 20% compared to the salty taste of the gastrointestinal tract preparation composition had the taste-modifying substance not been provided. The step to determine the pH of the gastrointestinal tract preparation composition can be carried out prior to or after the step of providing a taste-modifying substance to the patient.

The taste-modifying substance is preferably miraculin.

The desired pH range may be from about 1 to about 6.9, from about 2 to about 6.4, from about 2.5 to about 6.4, from about 3 to about 6.4, from about 4 to about 6.4, from about 5 to about 6.4, from about 3 to about 6, from about 3 to about 5.5, or from about 3 to about 5. In a preferred embodiment, the desired pH ranges from about 4.5 to about 5. In another preferred embodiment, the desired pH is about 4.8.

The gastrointestinal tract preparation composition of the present invention is administered orally, and may be used to prepare any part(s) of the gastrointestinal tract, including, but not limited to, the esophagus, stomach, intestine (or bowel) such as the small intestine and the large intestine including cecum, colon and rectum. For example, the present methods may be used to empty the bowel.

The method of the present invention may be used to cleanse the gastrointestinal tract prior to a diagnostic, therapeutic and/or surgical procedure. Non-limiting examples of the surgical procedures include a colon surgery and a gastrointestinal tract surgery. Non-limiting examples of the diagnostic procedures include a barium enema examination, a capsule endoscopy, an endoscopy such as a colonoscopy or sigmoidoscopy. Colonoscopy can be conventional colonoscopy or virtual colonoscopy. Heiken et al., Virtual colonoscopy for colorectal cancer screening: current status, November 2005, *Cancer Imagine* (International Cancer Imaging Society), 5 (Spec No A): S133-S139. The method of the present invention may be used in the treatment of acute gastrointestinal infections, for example bacterial or viral gastroenteritis. Colon cleansing is also useful for preventing infection after surgery on the lower intestine.

The taste-modifying substance may be provided to the patient from about 1 minute to about 3 hours, from about 1 minute to about 2 hours, from about 5 minutes to about 2 hours, from about 5 minutes to about 1.5 hours, from about 5 minutes to about 1 hour, from about 5 minutes to about 45 minutes, from about 5 minutes to about 30 minutes, from about 5 minutes to about 15 minutes, or from about 10 minutes to about 15 minutes before the gastrointestinal tract preparation composition is administered.

The present invention also provides for a method for modifying the taste of a liquid composition. The method has the following steps: (a) determining the pH of the liquid composition which has an undesirable taste, and adjusting the pH to range from about 3 to about 6.4 if necessary (i.e., if the pH of the liquid composition falls outside of the range of from about 3 to about 6.4, or other desired pH ranges as disclosed herein); (b) providing a taste-modifying substance to a subject; and (c) providing the liquid composition to the subject, wherein the undesirable taste of the liquid composition is reduced by at least about 20% compared to the undesirable taste of the liquid composition had the taste-modifying substance not been provided. The step to determine the pH of the liquid composition can be carried out prior to or after the step of providing a taste-modifying substance to the subject.

The liquid compositions include, but are not limited to, gastrointestinal tract preparation compositions, oral care compositions and pharmaceutical compositions.

Perception of one or more tastes by a subject (such as a patient) may be assessed using suitable questionnaires or by personal interviews. For example, immediately after a subject consumes (or tastes) a gastrointestinal tract preparation composition (or other liquid compositions), he/she is asked to finish a questionnaire. In the questionnaire, the subject is required to judge the perceived salty taste (or other undesirable taste) intensity of the composition using, for example, a scale of 0 to 10 (or a scale of 0 to 100, a scale of 0 to 5, a scale of 0 to 9, etc.). The subject will be instructed that "0" represents "no intensity" or "minimal intensity" (i.e., no or minimal salty taste or other undesirable taste) whereas "10" (or "100" etc.) represents the "highest intensity" of the salty taste (or other undesirable taste).

As taste is inherently subjective, the questionnaire or interview described above gives taste ratings that can be compared on the same patient or subject. The reduction in the undesirable taste (e.g., the salty taste) may be assessed by comparing the patient's (or subject's) taste rating when a taste-modifying substance was provided with the one when a taste-modifying substance was not provided. For example, if the taste rating without a taste-modifying substance is $T_1$, and the taste rating with a taste-modifying substance is $T_2$, the percentage reduction in the undesirable taste may be calculated as follows:

$$(T_1-T_2)/T_1*100\%$$

The undesirable taste of a liquid composition may be reduced by at least about 20%, at least about 30%, at least about 40%, at least about 50%, at least about 60%, at least about 70%, at least about 80%, at least about 90%, compared to the undesirable taste of the liquid composition had the taste-modifying substance not been provided.

In some embodiments, the salty taste of the gastrointestinal tract preparation composition 30 may be reduced by at least about 20%, at least about 30%, at least about 40%, at least about 50%, at least about 60%, at least about 70%, at least about 80%, at least about 90%, compared to the salty taste of the gastrointestinal tract preparation composition had the taste-modifying substance not been provided.

One or more tastes can also be rated using the Thurstonian scale. A Thurstonian model is a latent variable model for describing the mapping of some continuous scale onto discrete, possibly ordered categories of response. In the model, each of these categories of response corresponds to a latent variable whose value is drawn from a normal distribution, independently of the other response variables and with constant variance. Lawless et al., (1984), Direct and indirect scaling of sensory differences in simple taste and odor mixtures, *J. Food Sci.,* 49, 44-51. Durlach, et al., (1969) Intensity Perception. I. Preliminary Theory of Intensity Resolution, *Journal of the Acoustical Society of America,* 46 (2): 372-383. Dessirier et al., 1998, Comparison of d' values for the 2-AFC (paired comparison) and 3-AFC discrimination methods: Thurstonian models, sequential sensitivity analysis and power, *Food Quality and Preference,* 10 (1): 51-58. Frijter, J. E. R., (1980) Three-stimulus procedures in olfactory psychophysics: an experimental comparison of Thurstone-Ura and three-alternative forced choice models of signal detection theory, *Perception & Psychophysics,* 28 (5): 390-7, Gridgement, N. T., (1970) A Reexamination of the Two-Stage Triangle Test for the Perception of Sensory Differences, *Journal of Food Science,* 35 (1). Frijters, J. E. R., (1979) The paradox of discriminatory nondiscriminators resolved, *Chemical Senses & Flavor* 4 (4): 355-8. Valentin et al., Taste-odour interactions in sweet taste perception, In: Spillane W J, editor, Optimising sweet taste in foods. Cambridge (UK): Woodhead Publishing; 2006: 66-84.

Other rating scales can also be used in the present invention, including, but not limited to, intensity scales, just-about-right (JAR) scales and hedonic scale. In intensity scales, intensity rating questions ask respondents to rate the strength of a sensory attribute, for example, its saltiness, on a scale from "low" to "high". In just-about-right scales, just-about-right questions ask respondents to rate whether the level of a sensory attribute, for example, its saltiness, is "too high", "just right" or "too low". Popper et al., The effect of attribute questions on overall liking ratings, *Food Quality and Preference*, 15 (2004) 853-858. Peryam et al., Advanced taste-test method, *Food Eng.*, 1952, 24:58-61. Lim et al., Derivation and Evaluation of a Labeled Hedonic Scale, *Chem. Senses*, 34: 739-751, 2009. Gregson, R. A. M., A Rating-Scale Method for Determining Absolute Taste Thresholds, *Journal of Food Science*, 1962, 27: 376-380.

An exemplary intensity scale and an exemplary five-point JAR scale are shown in Table 1.

TABLE 1

| Intensity (nine-point) | JAR (five-point) |
|---|---|
| Extremely weak | Much too weak |
| | A little too weak |
| | Just about right |
| | A little too strong |
| | Much too strong |
| Extremely strong | |

The intensity of saltiness, sweetness, palatability or other tastes can be rated on a line scale, e.g., an unstructured or structured line scale, or other suitable line scales. In one embodiment, the rating scale is a 10-cm (or any other suitable length) visual analog scale with the anchors being "none" and "extremely strong". All ratings reported in the visual analog scale are then converted to a 100-point scale by measuring the length of the segment marked by the test subject. Stevenson et al., Confusing tastes and smells: how odours can influence the perception of sweet and sour taste? *Chem. Senses*, 1999, 24: 624-635.

As used herein, the term "taste" refers to any taste including the five basic tastes (i.e., sweet, sour, salty, bitter and umami) and other tastes such as tart, alkaline, astringent, tangy, dry, sharp, cool, warm, hot, burning, acidic, spicy, pungent, kokumi, savory, tingling and/or metallic. Such taste shall include any and all taste(s) as well as any and all aftertaste(s). The list above is not all inclusive as one skilled in the art would recognize.

As used herein, the term "taste-modifying substance" or "taste-modifying agent" refers to any substance that is able to modify the perception of at least one taste during consumption of a gastrointestinal tract preparation composition (or a liquid composition). They may act to modify the perception of a taste or may affect the taste profile. The term "modify" means to change, alter, modulate, diminish, lessen, reduce, subdue, limit, intensify, supplement or potentiate. For example, a sour taste-modifying agent may modify the perception of a sour taste; a salty-modifying agent may modify the perception of a salty taste. A taste-modifying substance may or may not possess a taste(s) of its own.

A taste-modifying substance may function by modulating the activity of taste receptor cells and/or the taste signaling pathway in a mammal. Specifically, taste is perceived through sensory cells located in the taste buds. Different signaling mechanisms sense the primary tastes of salty, sour, sweet, bitter and umami. Eventually a nerve impulse is triggered in the brain that is sensed as one of these primary tastes. For instance, in some cases, taste-modifying substances may bind to taste receptors, such as sweet taste receptors, which thereby modify the perception of the sweet taste. In other embodiments, taste-modifying substances may block taste receptors, such as salty receptors, which suppress the perception of a salty taste.

In some embodiments, the blocking of an undesirable taste may allow an increased sensation of another taste. For example, an increased sweet sensation that is perceived by the addition of a taste-modifying substance may diminish a salty taste.

The effect of a taste-modifying substance to modify the perception of a taste may or may not depend on its concentration. A taste-modifying substance may be used alone or in combination with other taste-modifying substance(s). When two or more taste-modifying substances are used, they may act additively or synergistically.

There may exist differences in taste perception between individuals. For example, there can be more than one perception of a single taste, whether such taste is a basic taste or another taste. For example, there may be a number of different "salty" tastes that can be noted by some individuals. U.S. Pat. No. 6,015,792.

The taste-modifying substance of the present invention may be a sweet taste-modifying agent, a sour taste-modifying agent, a salty taste-modifying agent, a bitter taste-modifying agent, an umami taste-modifying agent, etc.

Non-limiting examples of sweet taste-modifying agents include:

(a) protein: thaumatin, monellin, mabinlin, brazzein, pentadin, curculin, neuculin, miraculin and egg white lysozyme;

(b) water-soluble sweetening agents such as dihydrochalcones, stevia, steviosides, rebaudioside A, further steviol glycosides such as dulcoside and/or rubusoside, glycyrrhizin, dihydroflavenol; sugar alcohols (or polyols, such as sorbitol, mannitol, maltitol, xylitol, glycerol, erythritol, galactitol, hydrogenated isomaltulose, lactitol, hydrogenated starch hydrolysate, L-aminodicarboxylic acid aminoalkenoic acid ester amides, and mixtures thereof); monosaccharides, including but not limited to, aldoses and ketoses beginning with trioses such as glucose, galactose, and fructose; compounds generically known as sugars including, but not limited to, mono-, di- and oligosaccharides such as sucrose, maltose, lactose, etc; carbohydrates and polysaccharides including, but not limited to, polydextrose and maltodextrin;

(c) water-soluble artificial sweeteners such as soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1, 2,3-oxathiazine-4-one-2,2-dioxide (Acesulfame-K), the free acid form of saccharin, 1,6-dichloro-1,6-dideoxy-beta-D-fructofuranoysl-4-chloro-4-deoxy-alpha-D-galactopyran oside (Sucralose), 6-methyl-1,2,3-oxathiazin-4(3H)-one 2,2-dioxide (Acesulfame), cyclohexylsulfamic acid (Cyclamatee), N-(L-aspartyl)-N'(2,2,5,5,tetramethylcyclopentanoyl)1,1-diaminoethane and its related compounds, guanidinium class sweeteners, dihydrochalcone class sweeteners, stevioside, and their physiologically acceptable salts, and mixtures thereof;

(d) dipeptide based sweeteners, such as L-aspartic acid derived sweeteners, such as L-aspartyl-L-phenylalanine methyl ester (Aspartame), L-alphaaspartyl-N-(2, 2,4,4-tetramethyl-3-thietanyl)-D-alaninamide hydrate (Alitame), N—[N-(3,3-dimethylbutyl)-L-aspartyl]-L-phenylalanine 1-methyl ester (Neotame), methyl esters of L-aspartyl-L-phenylglycerine and L-aspartyl-L-2,5-dihydrophenyl-glycine, L-aspartyl-2,5-dihydro-L-phenylalanine; L-aspartyl-L-(1-cyclohexen)-alanine, and mixtures thereof;

(e) water-soluble sweeteners derived from naturally occurring water-soluble sweeteners, such as chlorinated derivatives of ordinary sugar (sucrose), e.g., chlorodeoxysugar derivatives such as derivatives of chlorodeoxysucrose or chlorodeoxygalactosucrose, known, for example, under the product designation of Sucralose; examples of chlorodeoxysucrose and chlorodeoxygalactosucrose derivatives include but are not limited to: 1-chloro-1'-deoxysucrose; 4-chloro-4-deoxy-alpha-D-galactopyranosyl-alpha-D-fructo furanoside, or 4-chloro-4-deoxygalactosucrose; 4-chloro-4-deoxy-alpha-D-galactopyranosyl-1-chloro-1-deoxy-beta-D-fructo-furanoside, or 4,1'-dichloro-4,1'-dideoxygalactosucrose; 1',6'-dichloro 1',6'-dideoxysucrose; 4-chloro-4-deoxy-alpha-D-galactopyranosyl-1,6-dichloro-1,6-dideoxy-beta-D-fructofuranoside, or 4,1',6'-trichloro-4,1',6'-trideoxygalactosucrose; 4,6-dichloro-4,6-dideoxy-alpha-D-galactopyranosyl-6-chloro-6-deoxy-beta-D-fructofuranoside, or 4,6,6'-trichloro-4,6,6'-trideoxygalactosucrose; 6,1',6'-trichloro-6,1',6'-trideoxysucrose; 4,6-dichloro-4,6-dideoxy-alpha-D-galacto-pyranosyl-1,6-dichloro-1,6-dideo-xy-beta-D-fructofuranoside, or 4,6,1',6'-tetrachloro-4,6,1',6'-tetradeoxygalacto-sucrose; and 4,6,1',6'-tetradeoxy-sucrose, and mixtures thereof.

Additional, non-limiting examples of the sweet taste-modifying substance include oslandin, polypodoside A, strogin, selligueanin A, dihydroquercetin-3-acetate, perillartin, telosmoside $A_{15}$, periandrin I-V, pterocaryosides, cyclocaryosides, mukuroziosides, trans-anethol, trans-cinnamaldehyde, bryosides, bryonosides, bryonodulcosides, camosiflosides, scandenosides, gypenosides, trilobtain, phloridzin, dihydroflavanols, hematoxylin, cyanin, chlorogenic acid, albiziasaponin, telosmosides, gaudichaudioside, mogrosides, hernandulcin, glycyrrhetinic acid, monoammonium glycyrrhizinate, licorice glycyrrhizinates, citrus aurantium, alapyridaine, alapyridaine (N-(1-carboxyethyl)-6-(hydroxymethyl)pyridinium-3-ol) inner salt, gymnemic acid, cynarin, glupyridaine, pyridinium-betain compounds, neohesperidin dihydrochalcone, trehalose, vanilla oleoresin, vanillin, monatin (2-hydroxy-2-(indol-3-ylmethyl)-4-aminoglutaric acid) and its derivatives; Lo han guo (also referred to as "Lo han kuo"); Furaneol (2,5-dimethyl-4-hydroxy-3(2H)-furanone) and derivatives (e.g. homofuraneol, 2-ethyl-4-hydroxy-5-methyl-3(2H)-furanone), homofuronol (2-ethyl-5-methyl-4-hydroxy-3(2H)-furanone and 5-ethyl-2-methyl-4-hydroxy-3(2H)-furanone), maltol and derivatives (e.g. ethylmaltol), coumarin and derivatives, gamma-lactones (e.g. gamma-undecalactone, gamma-nonalactone), delta-lactones (e.g. 4-methyldeltalactone, massoilactone, deltadecalactone, tuberolactone), methyl sorbate, divanillin, 4-hydroxy-2(or 5)-ethyl-5(or 2)-methyl-3(2H) furanone 2-hydroxy-3-methyl-2-cyclopentenones, 3-hydroxy-4,5-dimethyl-2(5H)-furanone, fruit esters and fruit lactones (e.g. acetic acid-n-butyl ester, acetic acid isoamyl ester, propionic acid ethyl ester, butyric acid ethyl ester, butyric acid-n-butyl ester, butyric acid isoamyl ester, 3-methyl-butyric acid ethyl ester, n-hexanoic acid ethyl ester, n-hexanoic acid allyl ester, n-hexanoic acid-n-butyl ester, n-octanoic acid ethyl ester, ethyl-3-methyl-3-phenylglycidate, ethyl-2-trans-4-cis-decadienoate), 4-(p-hydroxyphenyl)-2-butanone, 1,1-dimethoxy-2,2,5-trimethyl-4-hexane, 2,6-dimethyl-5-hepten-1-al, 4-hydroxycinnamic acid, 4-methoxy-3-hydroxycinnamic acid, 3-methoxy-4-hydroxycinnamic acid, 2-hydroxycinnamic acid, vanillic acid, homovanillic acid, vanillomandelic acid and phenylacetaldehyde; monoammonium glycyrrhizinate, licorice glycyrrhizinates, citrus aurantium, alapyridaine, alapyridaine (N-(1-carboxyethyl)-6-(hydroxymethyl)pyridinium-3-ol) inner salt, gymnemic acid, glupyridaine, pyridinium-betain compounds, neotame, neohesperidin dihydrochalcone, tagatose, trehalose, compounds that respond to G-protein coupled receptors (T2Rs and T1Rs), 2-hydroxybenzoic acid (2-HB), 3-hydroxybenzoic acid (3-HB), 4-hydroxybenzoic acid (4-HB), 2,3-dihydroxybenzoic acid (2,3-DHB), 2,4-dihydroxybenzoic acid (2,4-DHB), 2,5-dihydroxybenzoic acid (2,5-DHB), 2,6-dihydroxybenzoic acid (2,6-DHB), 3,4-dihydroxybenzoic acid (3,4-DHB), 3,5-dihydroxybenzoic acid (3,5-DHB), 2,3,4-trihydroxybenzoic acid (2,3,4-THB), 2,4, 6-trihydroxybenzoic acid (2,4,6-THB), 3,4,5-trihydroxybenzoic acid (3,4,5-THB), 4-hydroxyphenylacetic acid, 2-hydroxyisocaproic acid, 3-hydroxycinnamic acid, 3-aminobenzoic acid, 4-aminobenzoic acid and combinations thereof.

The naturally occurring sweeteners above can also be in the form of extracts or concentrated fractions of these extracts, in particular *Thaumatococcus* extracts (Katemfe bush), extracts of *Stevia* ssp. (in particular *Stevia rebaudiana*), Swingle extract (*Momordica* or *Siratia grosvenorii*, Lo han guo), extracts of licorice root, also *Glycerrhyzia* ssp. (in particular *Glycerrhyzia glabra*), *Rubus* ssp. (in particular *Rubus suavissimus*), citrus extracts, extracts of *Lippia dulcis*, vanilla extract, sugar beet extract, sugarcane leaf essence, correspondingly concentrated fractions of these extracts. U.S. Pat. No. 7,851,005. U.S. Patent Publication No. 20110076239. Kant, Sweet proteins—Potential replacement for artificial low calorie sweeteners, *Nutrition Journal* 2005, 4:5. I. Faus, Recent developments in the characterization and biotechnological production of sweet-tasting proteins, *Appl. Microbiol. Biotechnol.* 2000, 53: 145-151.

The taste-modifying substance may be water-soluble (i.e., capable of being substantially or completely dissolvable in water) or water-insoluble (i.e., exhibiting poor or no solubility in water). In some embodiments, it may be desirable to control the release rate of the taste-modifying substance. Different release rates may be desired depending on the type of the gastrointestinal tract preparation composition and the consumption time thereof. In some embodiments, the release rate may be based on the solubility of the taste-modifying substance in water, or based on the formulation of the composition containing the taste-modifying substance.

The taste-modifying substance may be used alone or as part of a composition, and in any suitable forms well-known in the art, including, but not limited to, free forms, spray-dried forms, powders, beads, liquids, solids, solutions, emulsions, dispersions, encapsulated forms, capsules, tablets, pills, granules, pellets, solids mixtures, gums, lozenges, dispersions in liquid phases, pastes, extracts, fractions or isolates obtained from natural sources and mixtures thereof.

The composition containing the taste-modifying substance may have at least one pharmaceutical carrier according to conventional pharmaceutical techniques. The carrier may take a wide variety of forms depending on the form of the composition. For example, for liquid oral formulations, such as suspensions, elixirs and solutions, suitable carriers and additives include water, glycols, oils, alcohols, flavoring agents, preservatives, coloring agents and the like. For solid oral formulations, such as powders, capsules and tablets, suitable carriers and additives include starches, sugars, diluents, granulating agents, lubricants, binders, disintegrating agents and the like.

The taste-modifying substance may be present in amounts ranging from about 0.01% to about 100%, from about 0.1% to about 90%, from about 1% to about 80%, from about 5% to about 70%, from about 5% to about 60%, from about 5% to about 50%, from about 5% to about 40%, or from about 5% to about 30% by weight of the composition containing the taste-modifying substance.

The taste-modifying substance may be kept in the subject's (e.g., patient's) mouth for about 5 seconds to about 30 minutes, about 10 seconds to about 20 minutes, about 15 seconds to about 10 minutes, about 30 seconds to about 5 minutes, about 1 minute to about 5 minutes, about 2 minutes to about 10 minutes, about 1 minutes to about 3 minutes. The composition containing the taste-modifying substance may disintegrate or dissolve in the subject's mouth. The taste-modifying substance may be applied to the subject's tongue. The taste-modifying substance (or the composition containing the taste-modifying substance) may also be chewed.

Miraculin can be considered both a sweet taste-modifying agent and a sour taste-modifying agent. In the present invention, miraculin may be from the miracle fruit, flesh of miracle fruit, miracle fruit granules, miracle berry, miracle berry extracts, frozen miracle berry, frozen miracle berry extract, dehydrated miracle berry, miracle fruit in powder form, miracle fruit tablets, miracle fruit gum, and miracle berry lollypop. Miraculin may also be produced from any suitable genetically modified cells or organism, including, but not limited to, *Escherichia coli*, yeast, plants (such as tobacco, lettuce, tomato, etc.), insect cells, and mammalian cells.

Miraculin can also be prepared using the methods described in U.S. Patent Publication No. 20090205068; U.S. Pat. No. 5,886,155; Theerasil et al., Complete Purification and Characterization of the Taste-modifying Protein, Miraculin, from Miracle Fruit, *J. Biol. Chem.* 1988, Vol. 263, No. 23: 11536-11539; Chen et al., The Sour Taste-Modifying Protein (Miraculin), Tyrosinase Inhibitors and Antioxidants from *Synsepalum dulcificum, Current Nutrition & Food Science,* 2009, 5, 172-179; Matsuyama et al., 2009, Functional expression of miraculin, a taste-modifying protein in *Escherichia coli, J. Biochem.* 145 (4): 445-50; Sun et al., Functional expression of the taste-modifying protein, miraculin, in transgenic lettuce, *FEBS Lett.* 2006, 580 (2): 620-6; Kato et al., Molecular Breeding of Tomato Lines for Mass Production of Miraculin in a Plant Factory. *J. Agric. Food Chem.* 2010, 58 (17): 9505-10.

The gastrointestinal tract preparation composition of the present invention is administered orally, and may be used to prepare any part(s) of the gastrointestinal tract, including, but not limited to, the esophagus, stomach, intestine (or bowel) such as the small intestine and the large intestine including cecum, colon and rectum.

Bowel preparation compositions, also called bowel cleansers, bowel cleansing compositions purgatives, cathartics, and lavages, are formulated for rapid emptying of the bowel and are intended for short-term use. Bowel preparation compositions include, for example, colon evacuants and colon cleansing compositions.

The gastrointestinal tract preparation composition of the present invention may be isosmotic or hyperosmotic. The gastrointestinal tract preparation composition may contain one or more electrolytes. The gastrointestinal tract preparation composition may contain at least one salt, including, but not limited to, a sodium salt, a potassium salt, a calcium salt, an ammonium salt or mixtures thereof. For example, the salts may be sodium chloride, potassium chloride, sodium bicarbonate (sodium hydrogen carbonate), sodium sulfate, sodium phosphate or mixtures thereof. The preparation composition may comprise at least one alkali metal salt, and/or at least one alkaline earth metal salt. The alkali metal may be sodium, potassium, etc. The alkaline earth metal may be magnesium, calcium, etc.

The gastrointestinal tract preparation composition may contain at least one sodium phosphate. The composition may have sodium phosphate in varying proportions of monobasic and dibasic species.

The concentration of the salt in the gastrointestinal tract preparation composition of the invention may vary depending on the type of the salt and other factors. For example, a liter of the preparation composition may contain greater than about 0.2 g, greater than about 0.5 g, greater than about 1 g, greater than about 2 g, greater than about 3 g, greater than about 5 g, less than about 10 g, less than about 9 g, less than about 7.5 g, less than about 7 g, less than about 5 g, less than about 4 g, less than about 2 g, less than about 1.5 g of a salt.

The gastrointestinal tract preparation composition may comprise polyethylene glycol (PEG). The PEG may comprise any food-grade or pharmaceutical-grade PEG. The average molecular weight of PEG may be greater than about 900, greater than about 2000, greater than about 2500, less than about 4500, or between about 3000 and about 8000. For example, it may be PEG 4000 or PEG 3350. PEG may also be lower molecular weight PEG polymers (such as PEG 400). The PEG used in a composition of the invention may comprise one PEG species, or two or more different PEG species.

The concentration of PEG in the gastrointestinal tract preparation composition of the invention may vary. A liter of the gastrointestinal tract preparation composition of the invention may contain greater than about 90 g, greater than about 100 g, less than about 250 g, less than about 150 g, less than about 140 g, or less than about 125 g of PEG. For example, a composition of the invention may comprise 100 g or 125 g per liter of PEG.

The gastrointestinal tract preparation composition may be administered over a time period ranging from about 30 minutes to about 3 days, from about 1 hour to about 24 hours, from about 2 hours to about 12 hours, or from about 1 hour to about 4 hours. The administration time period may be in a continuous period or a discontinuous period. In discontinuous administrations, a portion of the composition, for example, approximately half, may be administered the evening before the diagnostic, therapeutic or surgical procedure is to be carried out, with the remainder of the composition being administered on the day of the procedure. The preparation composition may be taken once or several times per day on the day of the diagnostic, surgical or therapeutic procedure, and/or on the day(s) preceding the procedure, depending upon various factors, such as the procedure, the degree of cleansing required, the patient's condition (e.g., the presence of complicating bowel conditions such as constipation).

A patient may take the taste-modifying substance every time before taking the gastrointestinal tract preparation composition, or may only take the taste-modifying substance before taking certain portions of the preparation composition.

The gastrointestinal tract preparation composition may be a liquid or a solid.

When it is a liquid (e.g., a solution), the dose or volume of the gastrointestinal tract preparation composition to be administered will depend on the patient being treated. For example, a smaller dose or volume of preparation solution is appropriate in the treatment of small children and a higher volume of preparation solution is appropriate in adult patients. When the gastrointestinal tract preparation composition is a liquid, the volume of the preparation composition administered may range from about 0.1 liters to about 5 liters, from about 0.2 liters to about 4.5 liters, from about 0.5 liters to about 4 liters, from about 1 liter to about 4 liters, from about 1 liter to about 3 liters, or from about 1.5 liters to about 2 liters. A patient may be required to finish all the gastrointestinal tract preparation composition, or may be asked to take the preparation composition until, for example, the rectal effluent is clear.

When the gastrointestinal tract preparation composition is a solution, it may have any suitable osmolarity, for example, greater than about 330 mOsmol/kg, greater than about 350 mOsmol/kg, greater than about 400 mOsmol/kg, greater than about 460 mOsmoL/kg, less than about 600 mOsmol/kg, less than about 550 mOsmol/kg, less than about 500 mOsmol/kg, less than about 470 mOsmol/kg.

The gastrointestinal tract preparation composition may also be concentrate compositions, such as, in dry form (e.g., powder, tablet, granular or any other suitable physical form) or in liquid form (e.g., syrup, suspension or emulsion). The bulk of the liquid component of a finished composition is not present in the concentrate to allow for reduced weight, volume, storage and shipping costs while at the same time allowing for increased shelf life of the concentrate versus final, diluted composition. When preparing the final, ready-to-administer composition, the concentrate composition may be diluted by any suitable liquid, such as water, tea, etc.

Non-limiting examples of the commercially available gastrointestinal tract preparation compositions include, but are not limited to, Colyte, GoLYTELY, NuLytely, TriLYTE, Half-Lytely, MoviPrep, and MiraLax, GlycoLax, Fleet Phospho-soda, Visicol, OsmoPrep, Fleet, Fleet Enema, Lo-So Prep, GlycoPrep C and Magnesium Citrate. U.S. Patent Publication Nos. 20100196513 and 20040170698. Technology Status Evaluation Report: Colonoscopy Preparation, *GASTROINTESTINAL ENDOSCOPY* 2009 69(7):1201-1209.

The present methods may also include administering additional agents to the patient. For example, for added potency in certain clinical applications, a bowel stimulant such as biscodyl or ascorbic acid, or other agent known for its laxative properties may be taken in conjunction with the administration of these compositions as appropriate.

The gastrointestinal tract preparation composition may contain at least one pharmaceutical carrier according to conventional pharmaceutical techniques. The carrier may take a wide variety of forms depending on the form of preparation desired for administration. For example, for liquid oral preparations such as, suspensions, elixirs and solutions, suitable carriers and additives include water, glycols, oils, alcohols, flavoring agents, preservatives, coloring agents and the like. For solid oral preparations such as, powders, capsules and tablets, suitable carriers and additives include starches, sugars, diluents, granulating agents, lubricants, binders, disintegrating agents and the like. In some embodiments, the composition may include optional additives such as antioxidants, amino acids, caffeine, emulsifiers, minerals, micronutrients, phytochemicals ("phytonutrients"), stabilizers, thickening agents, medicaments, vitamins, or mixtures thereof.

The pH of a gastrointestinal tract preparation solution (or a liquid composition) may be measured using conventional laboratory techniques, such as using a pH meter, pH sensor, pH indicator, pH test paper etc. In certain embodiments, it is also possible to calculate pH from knowledge of the components of a solution.

The gastrointestinal tract preparation solution may be acidified by at least an inorganic acid or an organic acid including, but not limited to, citric acid, acetic acid and ascorbic acid, phosphoric acid, malic acid, succinic acid, formic acid, fumaric acid, maleic acid, adipic acid, butyric acid, glyconic acid, lactic acid, oxalic acid, tartaric acid and mixtures thereof, or other permitted food acids.

The pH of the gastrointestinal tract preparation solution may also be adjusted by compounds including, but not limited to, ammonium hydroxide, sodium carbonate, potassium carbonate, sodium bicarbonate, carbon dioxide, and mixtures thereof.

When adjusting the pH of the composition, the pH may be increased or decreased by at least about 0.05 pH units, at least about 0.1 pH units, at least about 0.15 pH units, at least about 0.2 pH units, at least about 0.3 pH units, at least about 0.4 pH units, or at least about 0.5 pH units.

The present methods can be used with a mammal, preferably a human. Mammals include, but are not limited to, primates, simians, domestic animals, such as feline or canine subjects, farm animals, such as but not limited to bovine, equine, caprine, ovine, and porcine subjects, research animals, such as mice, rats, rabbits, goats, sheep, pigs, dogs, cats, etc.

The following examples of specific aspects for carrying out the present invention are offered for illustrative purposes only, and are not intended to limit the scope of the present invention in any way.

Example 1

Eleven subjects participated in the tasting experiment. All subjects were non-smokers with no known abnormalities in taste perception. No subject was on any medication which would alter taste perception.

The various tasting solutions (Nos. 1-3 as listed below) were prepared using commercially available colon prep, NuLytely (Braintree Laboratories Inc.). The NuLytely preparation was mixed according to the package insert using drinking water. According to the manufacturer's prescribing information, NuLytely powder contains 420 g polyethylene glycol 3350 (PEG-3350), 5.72 g sodium bicarbonate, 11.2 g sodium chloride, and 1.48 g potassium chloride. When made up to 4 liters volume with water, the solution contains 31.3 mmol/L PEG-3350, 65 mmol/L sodium, 53 mmol/L chloride, 17 mmol/L bicarbonate and 5 mmol/L potassium. Sample No. 1 contained only the NuLytely preparation; sample No. 2 contained the NuLytely preparation and the ingredients in the flavor pack that accompanied the NuLytely powder (provided by the manufacturer).

32 ounces of each sample were prepared on the day of the tasting experiment and the pH of each sample measured. The samples were kept refrigerated until the start of the tasting experiment.

The pH of the samples was measured using a digital waterproof pH meter, HM Digital pH meter PH-200. The pH meter was calibrated with a standard pH 7.0 reference solution made by General Hydroponics. The device was calibrated prior to measurements.

The pH of each sample was again measured 5 minutes prior to the start of the experiment. There was no change in the pH from the time of sample preparation. The solutions contained no precipitate.

The pH of tasting sample No. 3 was adjusted to 4.8 using a commercially available flavor pack. This flavor pack was a sugar-free, lemonade flavor packet, Kool-Aid unsweetened soft drink mix (Kraft). According to the manufacturer's packet insert, the powder in the flavor packet contained citric acid, calcium phosphate, maltodetrin, salt and less than 2% of natural flavor and preservatives. In addition to the lemonade flavor pack, 1.8 ml of commercially available lemon extract (McCormick & Co.) was added to the 4-liter NuLytely preparation mixture. The lemon extract contained alcohol, water and oil of Lemon. The pH was again checked after all the components were added and was confirmed to remain pH 4.8.

| | |
|---|---|
| No. 1: Original Nulytely prep with no flavor pack | pH 8.0 |
| No. 2: Nulytely prep with flavor pack | pH 8.0 |
| No. 3: Nulytely prep with lemonade powder and lemon extract | pH 4.8 |

Tasting Experiment

The eleven subjects each received 2 ounces of the sample and tasted it. They started with sample No. 1, followed by the remaining sample Nos. 2 through 3.

Tasting sample No. 3 was tasted with miracle berry tablets. The subjects were given one Mberry Miracle Fruit Tablet (400 mg per serving, distributed by My M Fruit LLC). An Mberry tablet contained miracle fruit powder and corn starch. The package instructions were followed and the tablet was placed on the subject's tongue and was allowed to dissolve in the mouth over a period of 5 minutes. After each tablet had completely dissolved, the subjects were given 2 ounces of the tasting sample.

For each of tasting sample Nos. 1-3, the sample was rated by the subjects in terms of saltiness. Each subject acted as their own control. The scale used to rate each sample was from 0 to 10. For saltiness, zero is the least salty and 10 very salty.

The subjects tasted every sample twice and rated saltiness each time. All of the ratings were recorded on a data collection sheet and kept blind to the other subjects.

The data sheets were collected from all eleven subjects. The average rating for saltiness for was calculated. See Table 2 and FIG. 1.

TABLE 2

| | No. 1 Nulytely | No. 2 Nulytely/ Provided Flavor Pack | No. 3 M Berry/ Lemonnade powder and lemon extract |
|---|---|---|---|
| Saltiness | 5.4 | 4.2 | 1.9 |

Results

The saltiness of the preparation solution was significantly diminished after the use of miracle berry.

Example 2

This study will involve the standard PEG colonoscopy preparation currently on the market with the addition of an unsweetened lemonade flavor pack which contains citric acid. The patient will be dissolving a freeze-dried Miracle fruit tablet on their tongue prior to consumption of the preparation, which will affect the patient's perception of taste.

Patient Selection

Patients scheduled for screening colonoscopies will be considered for the study. Patients may or may not have had previous colonoscopy. Patients with any abnormality or dysfunction in taste will be excluded from the study. Likewise exclusion criteria will also include patients who have had colonic, small bowel or gastric surgery as this may alter a patient's ability to tolerate the preparation. Patients with diagnosis of dry mouth, xerostomia, etc. will be excluded from the study. The indication for performing the colonoscopy should not be directed at specific diagnostic complaint but rather be indicated for the purpose of screening or surveillance. Patients with specific gastrointestinal complaints will be excluded from the study.

Study Design

At least one week prior to colonoscopy, patients taking a blood thinner, e.g., Coumadin, Plavix, must contact the ordering provider (e.g., a physician) for approval to stop the medication.

3 days prior to colonoscopy procedure, patients will be instructed to stop taking all herbal supplements, vitamins and iron; continue to take their daily prescribed medications, except for blood thinners as noted above; do not eat raw fruits or raw vegetables (cooked or canned fruit/vegetables are allowed); do not consume corn, peas, seeds, popcorn or nuts.

1 day prior to the procedure, 4-liter Colyte will be mixed and refrigerated if desired. Note Colyte must be ingested within 24 hours once mixed. Patients will not be allowed to begin to drink Colyte until 6 pm. The patients are instructed to drink clear liquids only all day, including breakfast, lunch and dinner. No solid food, dairy or alcohol will be allowed. Nothing red or purple will be allowed. The patients may have apple juice, white cranberry or grape juice, popsicles, jello, Italian ice, ginger ale, sprite, black coffee or tea, Gatorade. The patients need to drink 8 oz of clear liquid every hour between 11 am and 5 pm.

At 6 pm, the patients will drink one 8-oz glass of Colyte. The patients will be asked to complete a questionnaire rating the sweetness, saltiness and palatability of the Colyte preparation (FIG. 2), prior to adding a flavor packet or dissolving the miracle fruit tablet on the tongue.

After completion of the questionnaire in FIG. 2, the patients will add the flavor packet to the remaining Colyte preparation and mix well. The patients will then place one Miracle Berry tablet in the mouth and let it dissolve on the tongue over 3-5 minutes. The tablet cannot be chewed. This process of dissolving a tablet on the tongue will be repeated every 30 minutes during the time the patient is required to drink the preparation.

The patients will drink the first 8 oz of the newly mixed preparation, and then complete the second patient questionnaire, rating the sweetness, saltiness and palatability of the preparation (FIG. 3).

The patients will continue to drink one 8-oz preparation every 10 minutes until half of the 4-liter Colyte preparation solution is consumed. The remaining half of the preparation will be saved for drinking 5 hours prior to the procedure the next day. The consumption of half of the preparation likely will require between 1-4 miracle fruit tablets to be used every 30 minutes.

On the day of the procedure, 5 hours prior to the procedure, the patients will dissolve a miracle fruit tablet on the tongue over 3-5 minutes, and then drink 8 oz of Colyte. This will be repeated every 10 minutes until all the Colyte is consumed.

The patients will complete the post-preparation questionnaire (FIG. 4). Nothing is allowed in patients' mouth 2 hours prior to colonoscopy, not even clear liquid.

The patients will be instructed to take no diuretics or diabetic pills the morning of the colonoscopy procedure. Other prescribed medically necessary prescription can be taken with a sip of water at least 2 hours prior to colonoscopy. The patients need to have an adult 18 years or older to drive and accompany home.

Endoscopic Evaluation

Quality of colonic cleansing will be assessed by asking attending gastroenterologists in the outpatient endoscopy unit to complete a questionnaire immediately after the procedure designed to assess the quality of colonic mucosa visualization. Endoscopic visibility will be assessed for the amount of air bubbles in the colon and the adequacy of the colon preparation. The endoscopists will be instructed not to ask the patients about the details of their bowel preparations.

The questionnaire will ask the endoscopists to evaluate the quality of visualization as previously shown in S. Tongprasert et al., Improving Quality of Colonoscopy by Adding Simethicone to Sodium Phosphate Bowel Preparation, *World Journal of Gastroenterology*, 2009, 15(24): 3032-3037 and J. Johanson et al., A Randomized, Multicenter Study Comparing the Safety and Efficacy of Sodium Phosphate Tablets with 2 L Polyethylene Glycol Solution Plus Bisacodyl Tablets for Colon Cleansing, *American Journal of Gastroenterology*, 2007; 102: 2238-2246. The overall quality of visualization and the colonic cleansing will be based on (1) the amount of stool (liquid, semisolid, or solid) observed during the procedure and (2) the amount of "colonic contents" (including all liquid, semisolid, and solid material in the lumen of the colon) observed during the procedure rather than only "stool." Endoscopists will evaluate the visualization as follows: "excellent" means "small amounts of clear liquid, >90% mucosa seen, minimal suctioning needed for adequate visualization"; "good" means "residual liquid stool, >90% mucosa seen, significant suctioning needed for adequate visualization"; "adequate" means "some particulate matter, >90% of mucosa seen, mixture of liquid and semisolid stool which could be suctioned and/or washed"; "poor" means "substantial particulate matter or solid stool, <90% of mucosa seen, mixture of semisolid and solid stool, which could not be suctioned or washed"; and "unacceptable" means "solid stool through the colon."

Endoscopists will also be asked to estimate the amount of time they spent suctioning fluid and feces from the colon and time spent washing the colon to clean the mucosa relative to the total examination time. Endoscopists will be estimating the time spent suctioning and cleaning relative to the total examination time on a 4-degree scale: "0" means "almost no time spent, <2% of total examination time"; "1" means "minimal time spent, between 2%-8% of total examination time"; "2" means "some time spent, between 8%-15% of total examination time"; and "3" means "large amount of time spent, >15% of total examination time."

Five areas of the colon (rectosigmoid, descending, transverse, ascending, and cecum) will also be evaluated for the amount of air bubbles. As previously shown in S. Tongprasert et al., Improving Quality of Colonoscopy by Adding Simethicone to Sodium Phosphate Bowel Preparation, *World Journal of Gastroenterology*, 2009, 15(24): 3032-3037, the amount of intraluminal air bubbles will be classified into four grades: "0" means "no or minimal scattered bubbles"; "1" means "bubbles covering at least half the luminal diameter"; "2" means "bubbles covering the circumference of the lumen"; and "3" means "bubbles filling the entire lumen."

The success rate of the colonoscopies, total duration of colonoscopies and endoscopist satisfaction will be evaluated and compared between the two groups. Endoscopist satisfaction will be evaluated for air bubbles and adequacy of colon preparation by a self-rated questionnaire with a 4-degree scale: "0" means "very poor"; "1" means "poor"; "2" means "good"; and "3" means "very good."

Results

The results of this study will show that patients who took the gastrointestinal tract preparation with the miracle berry tablet complied with the requirements of the bowel preparation better than patients who took the preparation alone. These results will also show that the patients who took the gastrointestinal tract preparation solution with the miracle berry tablet had a more successful colonoscopy compared to those patients who took the preparation alone.

Tolerability and Satisfaction

The patients who have taken the gastrointestinal tract preparation solution with the miracle berry tablet will report that they ingested a significantly higher volume (e.g., 3.9 to 4 liters on average) of the fluid during the preparation period as compared to the patients who took the gastrointestinal tract preparation solution alone (e.g., 3 liters on average). The overall tolerability of the two preparation methods will also differ.

Not only will patients who have consumed the gastrointestinal tract preparation solution with the miracle berry tablet be more satisfied than patients who take the preparation alone, but also, patients who have consumed the gastrointestinal tract preparation solution with the miracle berry tablet will evaluate the preparation to be sweet and palatable and those who have consumed the preparation alone will evaluate the preparation to be foul-tasting and salty. In addition, endoscopists will also evaluate the colonoscopic examinations of patients who have consumed the gastrointestinal tract preparation solution with the miracle berry tablet to be more satisfactory compared to patients who have consumed the preparation without the miracle berry tablet. The data will be analyzed using standard statistical criteria.

Endoscopic Evaluation of Colonic Mucosa

Endoscopists who performed the colonoscopies will report that there is a difference in quality of visualization of the colonic mucosa between patients who took the gastrointestinal tract preparation solution with the miracle berry tablet(s) and those who took the preparation alone. The quality of colonic mucosa will be significantly better in the group of patients who took the gastrointestinal tract preparation solution with the miracle berry tablet(s) than in the group of patients who took the preparation alone. These endoscopists will report that there was clearer visualization of the colonic mucosa in patients who took the gastrointestinal tract preparation solution with the miracle berry tablet(s) compared to patients who took the preparation alone. They will also report that there were less intraluminal bubbles in areas of the colon in patients from the former group than the latter group and less time was spent suctioning fluid and feces from the colon and washing the colon to clean the mucosa. There will also be a higher success rate of completed colonoscopies and a shorter amount of time needed to complete the colonoscopy for patients who took the gastrointestinal tract preparation solution with the miracle berry tablet(s) than those who took the preparation alone.

Example 3

Four subjects, 30 to 55 years old, participated in the tasting experiment. They were three males and one female with no known abnormalities in taste perception. All subjects were non-smokers. No subject was on any medication which would alter taste perception.

The various tasting solutions (Nos. 1-6 as listed below) were prepared using a commercially available colon prep, HalfLytely (Braintree Laboratories Inc.). The HalfLytely preparation was mixed according to the package insert using drinking water. The flavor packet provided by the manufacturer was not used in the tasting experiment.

16 ounces of each sample were prepared the evening prior to the tasting experiment and the pH of each sample measured. The samples were kept refrigerated overnight until the start of the tasting experiment.

The pH of the samples was measured using a digital waterproof pH meter, HM Digital pH meter PH-200, with the below settings:

pH Range: 0-14
Temperature Range: 0-80° C.; 32-176° F.
Resolution: 0.01 pH; Temperature resolution is 0.1° C./F
Accuracy: +/−0.02 pH; Temperature accuracy is +/−2%
Calibration: Digital automatic calibration (one point) with digital fine tuning
Electrode: Replaceable glass sensor and reference tube electrodes
Housing: IP-67 Waterproof (submersible; floats)
Power source: 3×1.5V button cell batteries
Dimensions: 18.5×3.4×3.4 cm
Weight: 96.4 g (3.4 oz)

The pH meter was calibrated with a standard pH 7.0 reference solution made by General Hydroponics. The device was calibrated prior to measurements.

On the day of the tasting experiment, the pH of each sample was again measured 5 minutes prior to the start of the experiment. There was no change in the pH from the time of sample preparation the night prior. The solutions contained no precipitate after overnight storage.

The pH of the tasting samples was adjusted by using a commercial sugar-free, lemonade flavor packet, Kool-Aid unsweetened soft drink mix (Kraft). According to the manufacturer's packet insert, the powder in the flavor packet contained citric acid, calcium phosphate, maltodetrin, salt and less than 2% of natural flavor and preservatives. When necessary, the Kool-Aid powder was added to the tasting samples until the desired pH was reached. The pH in each of the six tasting samples was as follows:

| No. 1 Original prep with no Kool-Aid powder added | pH 8.0 |
| No. 2 Tasting sample | pH 7.0 |
| No. 3 Tasting sample | pH 6.0 |
| No. 4 Tasting sample | pH 5.0 |
| No. 5 Tasting sample | pH 4.0 |
| No. 6 Tasting sample | pH 3.0 |

Tasting Experiment:
Without Miracle Berry

The four subjects each received 2 ounces of the sample and tasted it. They started with the most basic solution above (sample No. 1, pH 8), followed by the remaining solutions 2 through 6. The sample was then rated by the subjects in terms of sweetness, saltiness and overall palatability. Each subject acted as their own control.

The scale used to rate each sample was from 0 to 10. For sweetness, zero is the least sweet and 10 very sweet; for saltiness, zero is the least salty and 10 very salty; for overall palatability, zero is the least palatable and 10 most palatable.

The subjects tasted every sample twice and rated sweetness, saltiness and overall palatability each time. All of the ratings were recorded on a data collection sheet and kept blind to the other subjects.

This arm of the experiment was conducted over a 20-minute time period.

Figure 5:
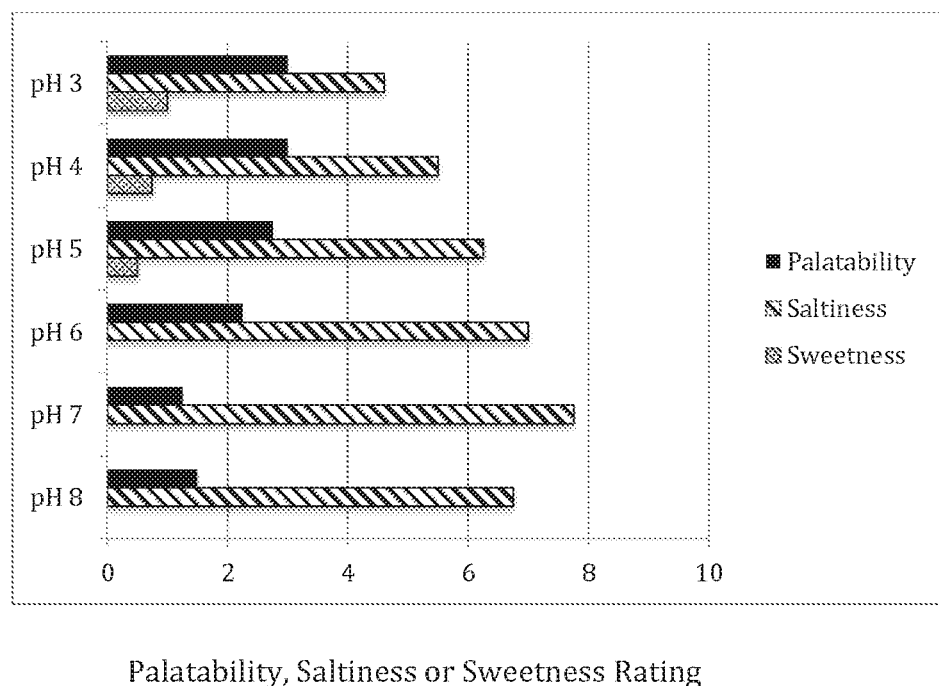
FIG. 5 shows the average rating in each of the three categories (sweetness, saltiness and overall palatability) for each of the six tasting samples after the four subjects tasted them without miracle berry tablets.

The data sheets were collected from all four subjects. The average rating in each of the three categories (sweetness, saltiness and overall palatability) for each of the tasting samples from the four subjects was calculated (Table 3 and FIG. 5)

TABLE 3

|  | pH 8 | pH 7 | pH 6 | pH 5 | pH 4 | pH 3 |
|---|---|---|---|---|---|---|
| Sweetness | 0 | 0 | 0 | 0.5 | 0.75 | 1 |
| Saltiness | 6.75 | 7.75 | 7 | 6.25 | 5.5 | 4.6 |
| Palatability | 1.5 | 1.25 | 2.25 | 2.75 | 3 | 3 |

With Miracle Berry

The four subjects were then given one Miracle Frooties tablet (600 mg per serving) produced by The Great Green Miracle Fruit Farm Ltd. A Miracle Frooties tablet contained the following: dried miracle fruit pulp, potato starch, microcrystalline cellulose, dibasic calcium phosphate and magnesium stearate.

The package instructions were followed and the miracle fruit tablet was placed on the subject's tongue and was allowed to dissolve in the mouth over a period of 5 minutes.

After each tablet had completely dissolved, tasting of the six tasting samples was again conducted as described above. The subjects were given 2 ounces of tasting samples and rated the samples according to sweetness, saltiness or overall palatability. The same 0-10 scale was used in this arm of the experiment. The ratings were recorded and kept blind to the other subjects.

This arm of the experiment was conducted over a 20-minute time period.

Figure 6:
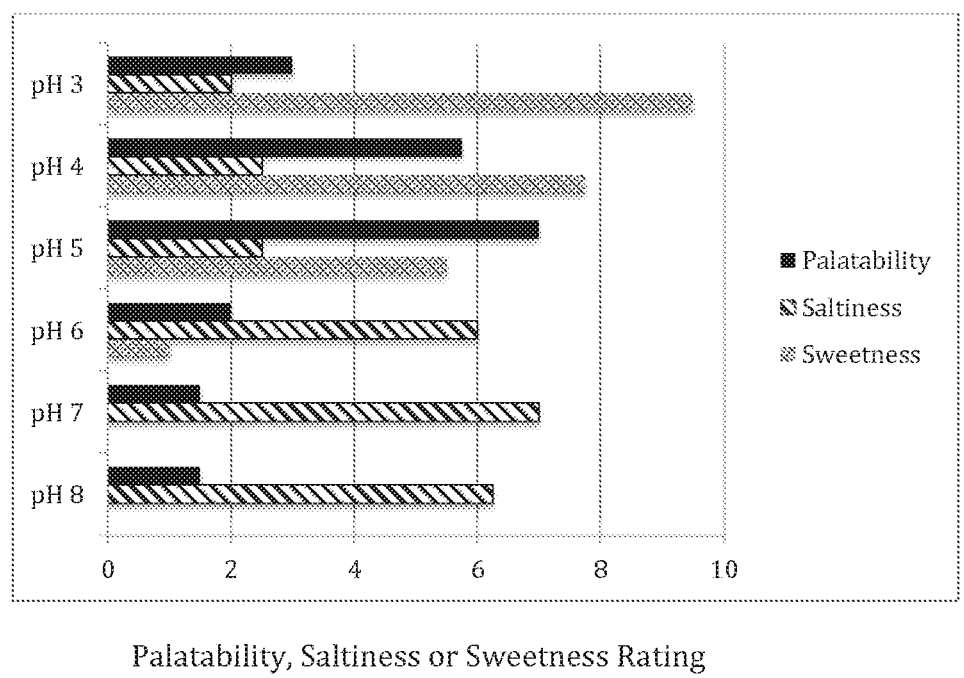
FIG. 6 shows the average rating in each of the three categories (sweetness, saltiness and overall palatability) for each of the six tasting samples after the four subjects tasted them with miracle berry tablets.

The data sheets were collected from all four subjects. The average rating in each of the three categories (sweetness, saltiness and overall palatability) for each of the tasting samples from the four subjects was again calculated (Table 4 and FIG. 6).

TABLE 4

|  | pH 8 | pH 7 | pH 6 | pH 5 | pH 4 | pH 3 |
|---|---|---|---|---|---|---|
| Sweetness | 0 | 0 | 1 | 5.5 | 7.75 | 9.5 |
| Saltiness | 6.25 | 7 | 6 | 2.5 | 2.5 | 2 |
| Palatability | 1.5 | 1.5 | 2 | 7 | 5.75 | 3 |

Results

The overall palatability of the preparation solution was greatly improved after the use of miracle berry tablet in an acidic environment. With miracle berry, the pH 5 solution was considered to be the most palatable prep solution.

The saltiness of the preparation solution was significantly diminished after the use of miracle berry with the pH solutions between 3-5 being considered the least salty.

The sweetness of the preparation solution was greatly improved after the use of miracle berry tablet in an acidic environment. With miracle berry, the pH 3 solution was considered to be the sweetest.

Example 4

Eleven subjects participated in the tasting experiment. All subjects were non-smokers, with no known abnormalities in taste perception. No subject was on any medication which would alter taste perception.

The various tasting solutions (Nos. 1-4 as listed below) were prepared using a commercially available colon prep, NuLytely (Braintree Laboratories Inc.). The NuLytely preparation was mixed according to the package insert using drinking water. According to the manufacturer's prescribing information, NuLytely powder contains 420 g polyethylene glycol 3350 (PEG-3350), 5.72 g sodium bicarbonate, 11.2 g sodium chloride, and 1.48 g potassium chloride. When made up to 4 liters volume with water, the solution contains 31.3 mmol/L PEG-3350, 65 mmoL/L sodium, 53 mmoL/L chloride, 17 mmol/L bicarbonate and 5 mmol/L potassium.

Sample No. 1 contained only the NuLytely preparation; sample No. 2 contained the NuLytely preparation and the ingredients in the flavor pack that accompanied the NuLytely powder (provided by the manufacturer).

32 ounces of each sample were prepared on the day of the tasting experiment and the pH of each sample measured. The samples were kept refrigerated until the start of the tasting experiment.

The pH of the samples was measured using a digital waterproof pH meter, HM Digital pH meter PH-200. The pH meter was calibrated with a standard pH 7.0 reference solution made by General Hydroponics. The device was calibrated prior to measurements.

The pH of each sample was again measured 5 minutes prior to the start of the experiment. There was no change in the pH from the time of sample preparation. The solutions contained no precipitate.

The pH of tasting sample Nos. 3 and 4 was adjusted to 4.8 by using a commercially available flavor pack. This flavor pack was a sugar-free, lemonade flavor packet, Kool-Aid unsweetened soft drink mix (Kraft). According to the manufacturer's packet insert, the powder in the flavor packet contained citric acid, calcium phosphate, maltodetrin, salt and less than 2% of natural flavor and preservatives. For sample No. 3, in addition to the lemonade flavor pack, 1.8 ml of commercially available lemon extract (McCormick & Co.) was added to the NuLytely 4-liter preparation mixture. For sample No. 4, in addition to the lemonade flavor pack, 1.8 ml of lemon extract (McCormick & Co.) and 1.8 ml of commercially available orange extract (McCormick & Co.) were added to the NuLytely 4-liter preparation mixture. The lemon extract (McCormick & Co.) contained alcohol, water and oil of lemon; the orange extract (McCormick & Co.) contained alcohol, water and oil of orange. The pH of tasting sample Nos. 3 and 4 was checked again after all the components were added and was confirmed to remain pH 4.8.

| | |
|---|---|
| No. 1: Original Nulytely prep with no flavor pack | pH 8.0 |
| No. 2: Nulytely prep with flavor pack | pH 8.0 |
| No. 3: Nulytely prep with lemonade powder and lemon extract | pH 4.8 |
| No. 4: Nulytely prep with lemonade powder and lemon/orange extracts | pH 4.8 |

Tasting Experiment

The eleven subjects each received 2 ounces of the sample and tasted it. They started with sample No. 1, followed by the remaining solutions 2 through 4.

Tasting sample Nos. 3 and 4 were tasted with miracle berry tablets. The subjects were given one Mberry, Miracle Fruit Tablet (400 mg per serving) distributed by My M Fruit LLC. An Mberry tablet contained miracle fruit powder and corn starch. The package instructions were followed and the miracle fruit tablet was placed on the subject's tongue and was allowed to dissolve in the mouth over a period of 5 minutes. After each tablet had completely dissolved, the subjects were given 2 ounces of the tasting samples.

For each sample tasting, the sample was rated by the subjects in terms of sweetness and overall palatability. Each subject acted as their own control. The scale used to rate each sample was from 0 to 10. For sweetness, zero is the least sweet and 10 very sweet; for overall palatability, zero is the least palatable and 10 most palatable.

The subjects tasted every sample twice and rated sweetness and overall palatability each time. All of the ratings were recorded on a data collection sheet and kept blind to the other subjects.

Figure 7:
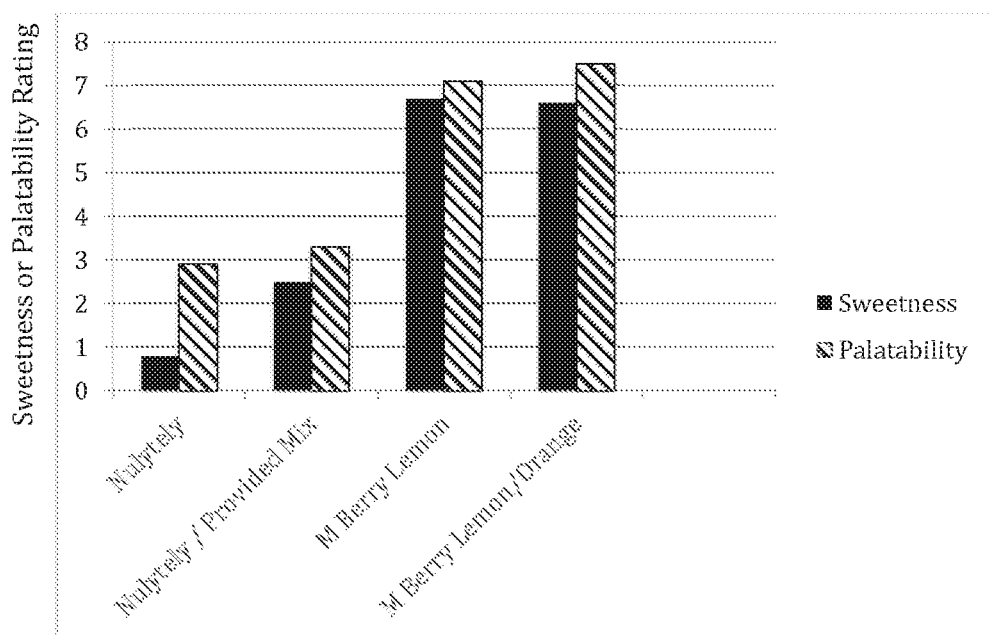
FIG. 7 is a graph for Example 5 demonstrating the average perception of sweetness and overall palatability for each of the 11 subjects with and without miracle berry tablets.

The data sheets were collected from all eleven subjects. The average rating in each of the two categories (sweetness and overall palatability) for each of the tasting samples from the eleven subjects was calculated. See Table 5 and FIG. 7.

TABLE 5

| | No. 1 Nulytely | No. 2 Nulytely/ Provided Mix | No. 3 M Berry Lemon | No. 4 M Berry Lemon/Orange |
|---|---|---|---|---|
| Sweetness | 0.8 | 2.5 | 6.7 | 6.6 |
| Palatability | 2.9 | 3.3 | 7.1 | 7.5 |

Results

The overall palatability and sweetness of the preparation solution were greatly improved after the use of miracle berry tablet in an acidic environment (e.g., pH 4.8 in this experiment).

The scope of the present invention is not limited by what has been specifically shown and described hereinabove. Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation.

The invention claimed is:

1. A method for reducing a salty taste of a liquid composition for a subject, the method comprising the steps of:
   (a) determining the pH of the liquid composition which has a salty taste, wherein the pH ranges from about 1 to about 6.9 or is adjusted to range from about 1 to about 6.9;
   (b) providing a taste-modifying substance to the subject, wherein the taste-modifying substance is selected from the group consisting of miraculin, thaumatin, monellin, mabinlin, brazzein, pentadin, curculin, neuculin, and mixtures thereof; and
   (c) administering the liquid composition to the subject after or when the taste-modifying substance is provided to the subject.

2. The method of claim 1, wherein the liquid composition is a gastrointestinal tract preparation composition to cleanse the gastrointestinal tract of the subject.

3. The method of claim 2, wherein the gastrointestinal tract is the intestine and the gastrointestinal tract preparation composition is a bowel preparation solution.

4. The method of claim 2, wherein the gastrointestinal tract is cleansed prior to carrying out a diagnostic, therapeutic and/or surgical procedure on the patient.

5. The method of claim 2, wherein the gastrointestinal tract is cleansed prior to an endoscopy.

6. The method of claim 5, wherein the endoscopy is a colonoscopy or sigmoidoscopy.

7. The method of claim 2, wherein the gastrointestinal tract is cleansed prior to a barium enema examination, capsule endoscopy, virtual colonoscopy, colon surgery or gastrointestinal tract surgery.

8. The method of claim 1, wherein the taste-modifying substance is miraculin.

9. The method of claim 8, wherein miraculin comprises miraculin fruit, flesh of miraculin fruit, miracle fruit granules, miracle berry, miracle berry extracts, miraculin fruit tablets, miraculin berry tablets, or miraculin produced by a genetically modified organism.

10. The method of claim 1, wherein the taste-modifying substance is provided in the form of a capsule, a tablet, a pill, granules, powders, a pellet, a solids mixture, a solution, a dispersion, an emulsion, a paste, an extract, or an isolate from a natural source.

11. The method of claim 1, wherein the taste-modifying substance is provided to the subject from about 1 minute to about 1 hour before the liquid composition is administered.

12. The method of claim 1, wherein the salty taste of the liquid composition is reduced by at least about 20% compared to the salty taste of the liquid composition had the taste-modifying substance not been provided.

13. The method of claim 1, wherein the pH ranges from about 3 to about 6.4.

14. The method of claim 1, wherein the pH ranges from about 4 to about 6.4.

15. The method of claim 2, wherein the gastrointestinal tract preparation composition comprises a potassium salt, a sodium salt, a calcium salt, an ammonium salt or mixtures thereof.

16. The method of claim 2, wherein the gastrointestinal tract preparation composition comprises at least one sodium phosphate.

17. The method of claim 2, wherein the gastrointestinal tract preparation composition comprises sodium chloride, potassium chloride, and sodium bicarbonate (sodium hydrogen carbonate), sodium sulfate or mixtures thereof.

18. The method of claim 2, wherein the gastrointestinal tract preparation composition comprises at least one alkali metal salt, and/or at least one alkaline earth metal salt.

19. The method of claim 18, wherein the alkali metal is sodium or potassium.

20. The method of claim 18, wherein the alkaline earth metal is magnesium or calcium.

21. The method of claim 2, wherein the gastrointestinal tract preparation composition is a solution, and wherein the volume of the gastrointestinal tract preparation composition ranges from about 0.1 liters to about 5 liters.

22. The method of claim 2, wherein the gastrointestinal tract preparation composition comprises polyethylene glycol (PEG).

* * * * *